United States Patent
Kamata (10) Patent No.: US 11,648,080 B2
(45) Date of Patent: May 16, 2023

(54) MEDICAL OBSERVATION CONTROL DEVICE AND MEDICAL OBSERVATION SYSTEM THAT CORRECT BRIGHTNESS DIFFERENCES BETWEEN IMAGES ACQUIRED AT DIFFERENT TIMINGS

(71) Applicant: Sony Olympus Medical Solutions Inc., Tokyo (JP)

(72) Inventor: Yoshiyuki Kamata, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/795,568

(22) Filed: Feb. 19, 2020

(65) Prior Publication Data

US 2020/0306002 A1 Oct. 1, 2020

(30) Foreign Application Priority Data

Mar. 25, 2019 (JP) .............................. JP2019-056834

(51) Int. Cl.
*A61B 90/00* (2016.01)
*A61B 34/00* (2016.01)
(Continued)

(52) U.S. Cl.
CPC .............. *A61B 90/36* (2016.02); *A61B 34/25* (2016.02); *A61B 34/74* (2016.02); *A61B 90/25* (2016.02);
(Continued)

(58) Field of Classification Search
CPC ...... G02B 21/367; A61B 2090/03; G06T 5/50; G06T 7/0014; G06T 7/11; G06T 7/0081; G06K 9/3233
See application file for complete search history.

(56) References Cited

U.S. PATENT DOCUMENTS

2004/0047518 A1* 3/2004 Tiana .................... G06T 5/50
382/284
2011/0028850 A1* 2/2011 Schuhrke ............. A61B 5/0261
600/476
(Continued)

FOREIGN PATENT DOCUMENTS

JP H07065146 A 3/1995
JP 2000041942 A 2/2000
(Continued)

*Primary Examiner* — Jayanti K Patel
*Assistant Examiner* — Christopher Kingsbury Glover
(74) *Attorney, Agent, or Firm* — Xsensus LLP (57) ABSTRACT

A medical observation control device and system include a memory that stores a parameter for a first imaging condition of an imager at a first time of capturing a first medical image and circuitry configured to correct for brightness differences between the first medical image captured at the first time and a second medical image captured at a second time. The circuitry is configured to restore the parameter for the first imaging condition as a second imaging condition for capturing the second medical image, control the imager so as to capture an image of an observation object under the second imaging condition as the second medical image, compare the first medical image with the second medical image, and correct brightness of at least one of brightness of the first medical image and brightness of the second medical image based on a comparison result.

17 Claims, 9 Drawing Sheets

(51) Int. Cl.
 G02B 21/36 (2006.01)
 A61B 90/25 (2016.01)
 G02B 21/02 (2006.01)

(52) U.S. Cl.
 CPC ......... G02B 21/025 (2013.01); G02B 21/367 (2013.01); *A61B 2034/743* (2016.02); *A61B 2034/744* (2016.02)

(56) References Cited

U.S. PATENT DOCUMENTS

| | | | |
|---|---|---|---|
| 2016/0180526 A1* | 6/2016 | Satoh | G06T 5/007 |
| | | | 382/131 |
| 2018/0092705 A1* | 4/2018 | Ootsuki | G02B 21/36 |
| 2020/0221037 A1* | 7/2020 | Lu | H04N 5/2353 |
| 2020/0288072 A1* | 9/2020 | Seok | H04N 5/332 |
| 2020/0329226 A1* | 10/2020 | Medal | G01S 5/163 |

FOREIGN PATENT DOCUMENTS

| | | | | |
|---|---|---|---|---|
| JP | 2004000505 A | 1/2004 | | |
| JP | 2009018116 A | 1/2009 | | |
| JP | 2015025965 A | 2/2015 | | |
| JP | 2018-029980 A | 3/2018 | | |
| WO | WO-2002067039 A1 | 8/2002 | | |
| WO | WO-2017122431 A1 | 7/2017 | | |
| WO | WO-2017169135 A1 * | 10/2017 | ............. | G02B 21/24 |

\* cited by examiner

MEDICAL OBSERVATION CONTROL DEVICE AND MEDICAL OBSERVATION SYSTEM THAT CORRECT BRIGHTNESS DIFFERENCES BETWEEN IMAGES ACQUIRED AT DIFFERENT TIMINGS

This application claims priority from Japanese Application No. 2019-056834, filed on Mar. 25, 2019, the contents of which are incorporated by reference herein in its entirety.

BACKGROUND

The present disclosure relates to a medical observation control device and a medical observation system.

In the related art, as a medical observation system for observing a minute part at the time of performing surgery on a minute part in a brain, heart, or the like of a patient to be observed, an optical microscope system including a support portion which includes a plurality of arm portions and realizes a movement of a total of six degrees of freedom including three degrees of freedom of translation and three degrees of rotation and a microscope unit which is provided in a front end portion of the support portion and includes a magnifying optical system or imaging element magnifying a minute part is known (for example, see JP 2018-29980 A). When surgery is performed using the microscope system, an operator (user) such as a doctor moves the microscope unit to be disposed at a desired position and performs surgery while observing a surgical site. In JP 2018-29980 A, the position of the microscope unit may be restored since the position or angle of the arm portion is memorized.

In recent years, an observation method for performing special light observation using special light separately from normal observation using white light has been devised. Specifically, examples of the special light observation include a technique called Narrow Band Imaging (NBI), a technique called Infra-Red Imaging (IRI), a technique called Auto Fluorescence Imaging (AFI), a technique called Photodynamic Diagnosis (PDD), and the like.

For example, in IRI, a drug called indocyanine green (ICG) having an absorption peak in near-infrared light around 805 nm in wavelength in blood is injected intravenously as a contrast agent, excitation light having a wavelength of about 750 to 810 nm is irradiated, fluorescence of about 840 nm is detected, a shadow of a blood vessel portion of a submucosal layer due to absorption of ICG is observed, and a running state of blood vessels and lymph vessels is diagnosed.

SUMMARY

Incidentally, in surgery with special light observation, images before and after surgery may be compared with each other. For example, in IRI, a blood flow or flow rate before and after surgery is checked from the images before and after surgery. At this time, in the images before and after surgery, various parameters relating to the image (parameters for a viewing angle or brightness) need to be the same. Even when the same image may be obtained before and after surgery by restoring the position of the microscope unit, an accurate comparison may not be performed when the brightness of the image changes due to a change in the illumination of the surgical site.

According to one aspect of the present disclosure, there is provided a medical observation control device including: a memory configured to store a parameter for a first imaging condition including a position of an imager at a time of capturing a first medical image; and circuitry configured to restore the parameter for the first imaging condition as a second imaging condition for capturing a second medical image, control the imager and a support configured to support the imager so as to capture an image of an observation object under the second imaging condition, compare the first medical image with the second medical image, and correct brightness of at least one of brightness of the first medical image and brightness of the second medical image based on a comparison result.

DETAILED DESCRIPTION

Hereinafter, a mode for carrying out the disclosure (hereinafter, referred to as "embodiments") will be described with reference to the accompanying drawings. Additionally, the drawings are merely schematic and parts having different dimensional relationships and ratios are different between the drawings.

First Embodiment

Figure 1:
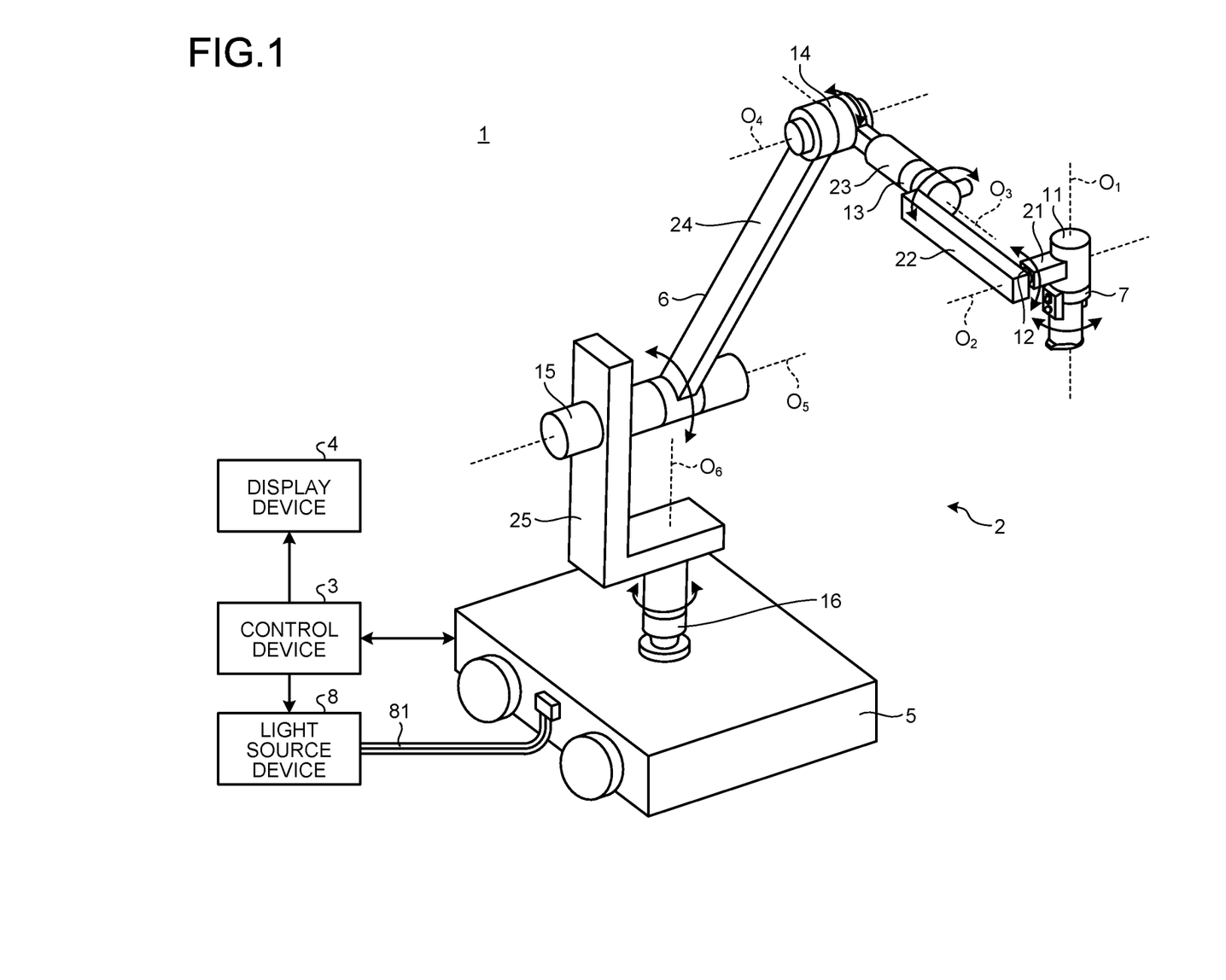
FIG. 1 is a perspective view illustrating an external configuration of a medical observation system according to a first embodiment.

FIG. 1 is a diagram illustrating a configuration of a medical observation system according to a first embodiment. A medical observation system 1 illustrated in FIG. 1 includes a medical observation apparatus (hereinafter, referred to as an observation apparatus) 2 which has a function as a microscope for magnifying and capturing a microstructure of an observation target, a control device 3 which controls an overall operation of the medical observation system 1, and a display device 4 which displays an image captured by the observation apparatus 2. The control device 3 corresponds to a medical observation control device.

The observation apparatus 2 includes a base portion 5 which is movable on a floor, a support portion 6 which is supported by the base portion 5, and a pillar microscope unit 7 which is provided in a front end of the support portion 6 and magnifies and captures a minute part of an observation target. Further, a light source device 8 which supplies illumination light to the observation apparatus 2 through a light guide 81 formed as an optical fiber or the like is connected to the observation apparatus 2. The light source device 8 emits white light or light (special light) in a wavelength band according to the special observation based on an observation mode under the control of the control device 3.

In the observation apparatus 2, for example, a cable group including a transmission cable with a signal line (a coaxial cable) for transmitting a signal between the control device 3 and the microscope unit 7 or a light guide cable for guiding illumination light from the light source device 8 to the microscope unit 7 is disposed from the base portion 5 to the microscope unit 7.

The support portion 6 includes a first joint portion 11, a first arm portion 21, a second joint portion 12, a second arm portion 22, a third joint portion 13, a third arm portion 23, a fourth joint portion 14, a fourth arm portion 24, a fifth joint portion 15, a fifth arm portion 25, and a sixth joint portion 16.

The first joint portion 11 rotatably holds the microscope unit 7 at the front end side and is held by the first arm portion 21 while being fixed to the front end portion of the first arm portion 21 at the proximal end side. The first joint portion 11 has a cylindrical shape and holds the microscope unit 7 so as to be rotatable around a first axis $O_1$ which is a center axis in the height direction. The first arm portion 21 has a shape extending from a side surface of the first joint portion 11 in a direction orthogonal to the first axis $O_1$.

The second joint portion 12 rotatably holds the first arm portion 21 at the front end side and is held by the second arm portion 22 while being fixed to the front end portion of the second arm portion 22 at the proximal end side. The second joint portion 12 has a cylindrical shape and holds the first arm portion 21 so as to be rotatable around a second axis $O_2$ which is a center axis in the height direction and is an axis orthogonal to the first axis $O_1$. The second arm portion 22 has a substantial L shape and is connected to the second joint portion 12 at the end portion of the L-shaped vertical line portion.

The third joint portion 13 rotatably holds the L-shaped horizontal line portion of the second arm portion 22 at the front end side and is held by the third arm portion 23 while being fixed to the front end portion of the third arm portion 23 at the proximal end side. The third joint portion 13 has a cylindrical shape and holds the second arm portion 22 so as to be rotatable around a third axis $O_3$ which is a center axis in the height direction, an axis orthogonal to the second axis $O_2$, and an axis parallel to the extension direction of the second arm portion 22. The third arm portion 23 is formed such that the front end side has a cylindrical shape and the proximal end side is provided with a hole portion penetrating in a direction orthogonal to the height direction of the cylinder of the front end side. The third joint portion 13 is rotatably held by the fourth joint portion 14 through the hole portion.

The fourth joint portion 14 rotatably holds the third arm portion 23 at the front end side and is held by the fourth arm portion 24 while being fixed to the fourth arm portion 24 at the proximal end side. The fourth joint portion 14 has a cylindrical shape and holds the third arm portion 23 so as to be rotatable around a fourth axis $O_4$ which is a center axis in the height direction and is an axis orthogonal to the third axis $O_3$.

The fifth joint portion 15 rotatably holds the fourth arm portion 24 at the front end side and is fixed and attached to the fifth arm portion 25 at the proximal end side. The fifth joint portion 15 has a cylindrical shape and holds the fourth arm portion 24 so as to be rotatable around a fifth axis $O_5$ which is a center axis in the height direction and is an axis parallel to the fourth axis $O_4$. The fifth arm portion 25 includes an L-shaped portion and a rod-shaped portion extending downward from the L-shaped horizontal line portion. The fifth joint portion 15 is attached to the L-shaped vertical line portion of the fifth arm portion 25 at the proximal end side.

The sixth joint portion 16 rotatably holds the fifth arm portion 25 at the front end side and is fixed and attached to the upper surface of the base portion 5 at the proximal end side. The sixth joint portion 16 has a cylindrical shape and holds the fifth arm portion 25 so as to be rotatable around a sixth axis $O_6$ which is a center axis in the height direction and is an axis orthogonal to the fifth axis $O_5$. A proximal end portion of a rod-shaped portion of the fifth arm portion 25 is attached to the front end side of the sixth joint portion 16.

The support portion 6 with the above-described configuration realizes a movement of the microscope unit 7 with a total of six degrees of freedom including three degrees of freedom of translation and three degrees of rotation.

The first joint portion 11 to the sixth joint portion 16 include electromagnetic brakes respectively prohibiting the rotation of the microscope unit 7 and the first arm portion 21 to the fifth arm portion 25. Each electromagnetic brake is released while an arm operation switch 73 (to be described later) provided in the microscope unit 7 is pressed down so that the rotation of the microscope unit 7 and the first arm portion 21 to the fifth arm portion 25 is allowed. Additionally, an air brake may be applied instead of the electromagnetic brake. Further, the first joint portion 11 may have a configuration without the electromagnetic brake.

An encoder and an actuator may be mounted on each joint portion in addition to the electromagnetic brake. For example, when the encoder is provided in the first joint portion 11, the rotation angle of the first axis $O_1$ is detected. The actuator is configured by, for example, an electric motor such as a servomotor and is driven by the control from the control device 3 so that the joint portion rotates by a predetermined angle. For example, the rotation angle of the joint portion is set by the control device 3 based on the rotation angle in each of the rotation axes (the first axis $O_1$ to the sixth axis $O_6$) as a value necessary for moving the microscope unit 7 so that an observation point does not change before and after the movement of the microscope unit 7. In this way, the joint portion provided with an active driving system such as an actuator constitutes a rotation axis actively rotating as the driving of the actuator is controlled.

The microscope unit 7 has a configuration in which an imaging unit magnifying and capturing an image of an observation target, an arm operation switch releasing the electromagnetic brake of the first joint portion 11 to the sixth joint portion 16 and receiving an operation input for allowing the rotation of each joint portion, and a change switch capable of changing a magnification of the imaging unit and a focal distance to the observation target are provided in a cylindrical casing.

The imaging unit includes two imaging elements configured by using a Charge Coupled Device (CCD) or a Complementary Metal Oxide Semiconductor (CMOS). These imaging elements respectively generate imaging signals for generating a 3D image and having parallax with each other. The imaging signal is output as a digital signal. Additionally, one imaging element may be provided to generate an imaging signal for generating a 2D image.

Further, the imaging unit is provided with an optical system which guides light to the imaging element, an optical system configured by one or a plurality of lenses for changing the magnification (zoom magnification) of the image, a shutter for controlling an exposure time, and the like.

Further, the microscope unit 7 is provided with an arm operation switch which is a push button type switch. While a user pressed down the arm operation switch, the electromagnetic brakes of the first joint portion 11 to the sixth joint portion 16 are released.

The control device 3 generates 3D image data for display by receiving an imaging signal output from the observation apparatus 2 and applying a predetermined signal process to the imaging signal. Additionally, the control device 3 may be provided inside the base portion 5 to be integrated with the observation apparatus 2.

Figure 2:
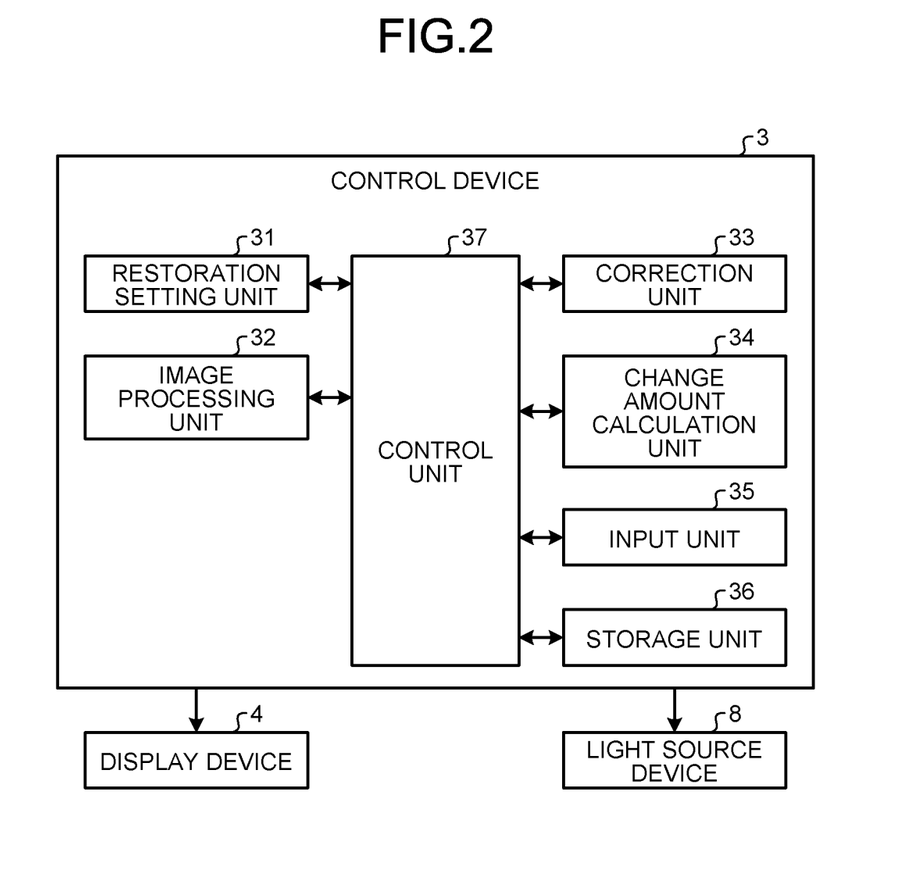
FIG. 2 is a block diagram illustrating a configuration of a control device of the medical observation system according to the first embodiment.

FIG. 2 is a block diagram illustrating a configuration of a control device of the medical observation system according to the first embodiment. The control device 3 includes a restoration setting unit 31, an image processing unit 32, a correction unit 33, a change amount calculation unit 34, an input unit 35, a storage unit 36, and a control unit 37. Additionally, the control device 3 may be provided with a power supply unit (not illustrated) which generates a power voltage for driving the control device 3 and the microscope unit 7, supplies the power voltage to each part of the control device 3, and supplies the power voltage to the microscope unit 7 through a transmission cable.

The restoration setting unit 31 stores restoration parameters at a time point when the condition holding is instructed in the storage unit 36 and reads out the restoration parameters stored in the storage unit 36 when the restoration is instructed so as to restore the imaging condition or the position of the microscope unit 7. As the restoration parameter, the illuminance of the light source, the shutter speed, the gain value, the focal distance, the zoom magnification, the aperture value of the lens, the position of the microscope unit 7 such as a posture of each arm portion (the rotation angle of the joint portion), and a parameter for restoring the imaging condition are exemplified.

The image processing unit 32 performs a signal process such as noise removal or A/D conversion if necessary on the imaging signal output from the microscope unit 7. The image processing unit 32 generates a display image signal displayed by the display device 4 based on the imaging signal subjected to the signal process. The image processing unit 32 generates a display image signal including an object image by performing a predetermined signal process on the imaging signal. Here, the image processing unit 32 performs known image processes including various image processes such as a detection process, an interpolation process, a color correction process, a color enhancement process, and a contour enhancement process. The image processing unit 32 outputs the generated image signal to the display device 4.

Further, the image processing unit 32 may include an AF processing unit which outputs a predetermined AF evaluation value of each frame based on the imaging signal of input frame and an AF calculation unit which performs an AF calculation process of selecting a focus lens position or a frame suitable as a focal position from the AF evaluation value of each frame from the AF processing unit.

The correction unit 33 compares luminance values of images captured at different timings, for example, a luminance value of a comparison region in an image before surgery and a luminance value of the comparison region in the image after surgery. The correction unit 33 calculates a difference in luminance value of the comparison region in two images. For example, the correction unit 33 calculates a representative value of each comparison region and calculates a difference of the representative values.

The comparison region is set through the input unit 35 or is set in advance for the viewing angle. In two images, the position for the viewing angle of the comparison image is the same.

The representative value is one of an added value, an average value, a mode value, a maximum value, and a minimum value of the pixel values in the comparison region.

Further, the correction unit 33 corrects a luminance value of a first image or a luminance value of a second image based on the calculated difference. The correction unit 33 corrects the luminance value of the second image, for example, based on the difference. Additionally, for example, when only the flow measurement is performed in the IRI, only the flow measurement position may be corrected.

The change amount calculation unit 34 calculates a brightness change amount from the first image and the second image after the correction of the correction unit 33. For example, when the blood flow rate measurement is performed in the IRI, the difference of the brightness (the luminance value) is calculated as a blood flow rate change amount.

The input unit 35 is realized using a user interface such as a keyboard, a mouse, and a touch panel and receives various kinds of information.

The storage unit 36 is realized using a semiconductor memory such as a flash memory or Dynamic Random Access Memory (DRAM) and stores communication information data (for example, communication format information or the like) or the restoration parameter. Additionally, the storage unit 36 may store various programs executed by the control unit 37.

The control unit 37 controls the driving of each of components including the control device 3 and the microscope unit 7 and controls the input and output of information for each of components. The control unit 37 generates a control signal by referring to the communication information data (for example, communication formation information or the like) stored in the storage unit 36 and transmits the generated control signal to the microscope unit 7. Further, the control unit 37 outputs a control signal to the microscope unit 7 through a transmission cable.

Additionally, the control unit 37 generates a synchronization signal and a clock for the microscope unit 7 and the control device 3. The synchronization signal (for example, a synchronization signal for instructing an imaging timing) or the clock (for example, a serial communication clock) for the microscope unit 7 is transmitted to the microscope unit 7 through a line (not illustrated) and the microscope unit 7 is driven based on the synchronization signal or clock.

The restoration setting unit 31, the image processing unit 32, the correction unit 33, and the control unit 37 are realized using a general-purpose processor such as a Central Processing Unit (CPU) having an internal memory (not illustrated) storing a program or a dedicated processor such as an arithmetic circuit executing a specific function such as an Application Specific Integrated Circuit (ASIC). Further, these units may be configured using a Field Programmable Gate Array (FPGA: not illustrated) which is a kind of programmable integrated circuit. Additionally, in the case of the configuration of the FPGA, a memory storing configuration data may be provided and the FPGA corresponding to a programmable integrated circuit may be configured by the configuration data read out from the memory.

The display device 4 receives 3D image data generated by the control device 3 from the control device 3 and displays a 3D image corresponding to the 3D image data. Such a display device 4 includes a display panel configured by a liquid-crystal or organic Electro Luminescence (EL).

Additionally, an output device outputting information using a speaker or a printer may be provided in addition to the display device 4.

Figure 3:
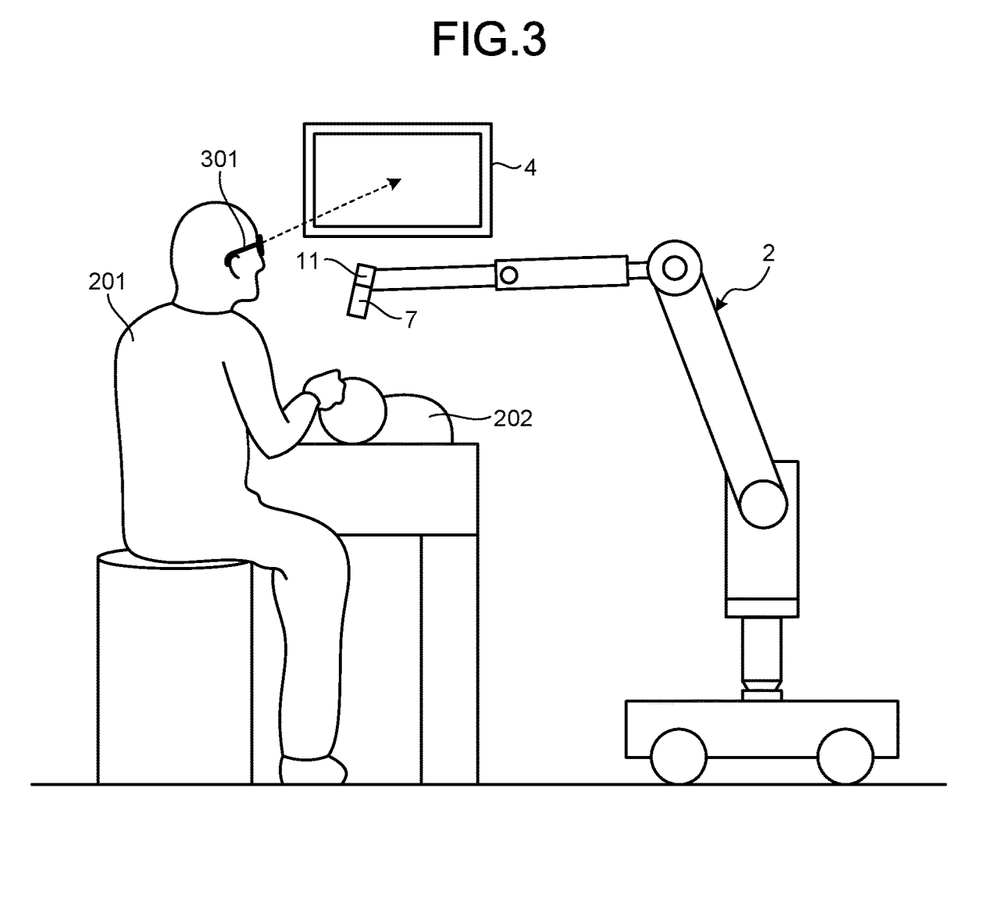
FIG. 3 is a diagram schematically illustrating a situation of surgery performed using the medical observation system according to the first embodiment.

Next, an outline of surgery performed using the medical observation system 1 with the above-described configuration will be described. FIG. 3 is a diagram schematically illustrating a situation of surgery using the medical observation system 1. Specifically, FIG. 3 is a diagram schematically illustrating a situation in which an operator 201 as a user is operating a head of a patient 202 who is an observation target. The operator 201 wears 3D image glasses 301, grips and moves the microscope unit 7 to a desired position while seeing a 3D image displayed by the display device 4 and pressing down the arm operation switch of the microscope unit 7, determines the imaging field of view of the microscope unit 7, and releases a finger from the arm operation switch. Accordingly, the electromagnetic brakes of the first joint portion 11 to the sixth joint portion 16 are operated and the imaging field of view of the microscope unit 7 is fixed. Then, the operator 201 adjusts the magnification and the focal length to the observation target. Since the display device 4 displays the 3D image, the operator 201 may three-dimensionally check a surgical site through the 3D image.

Figure 4:
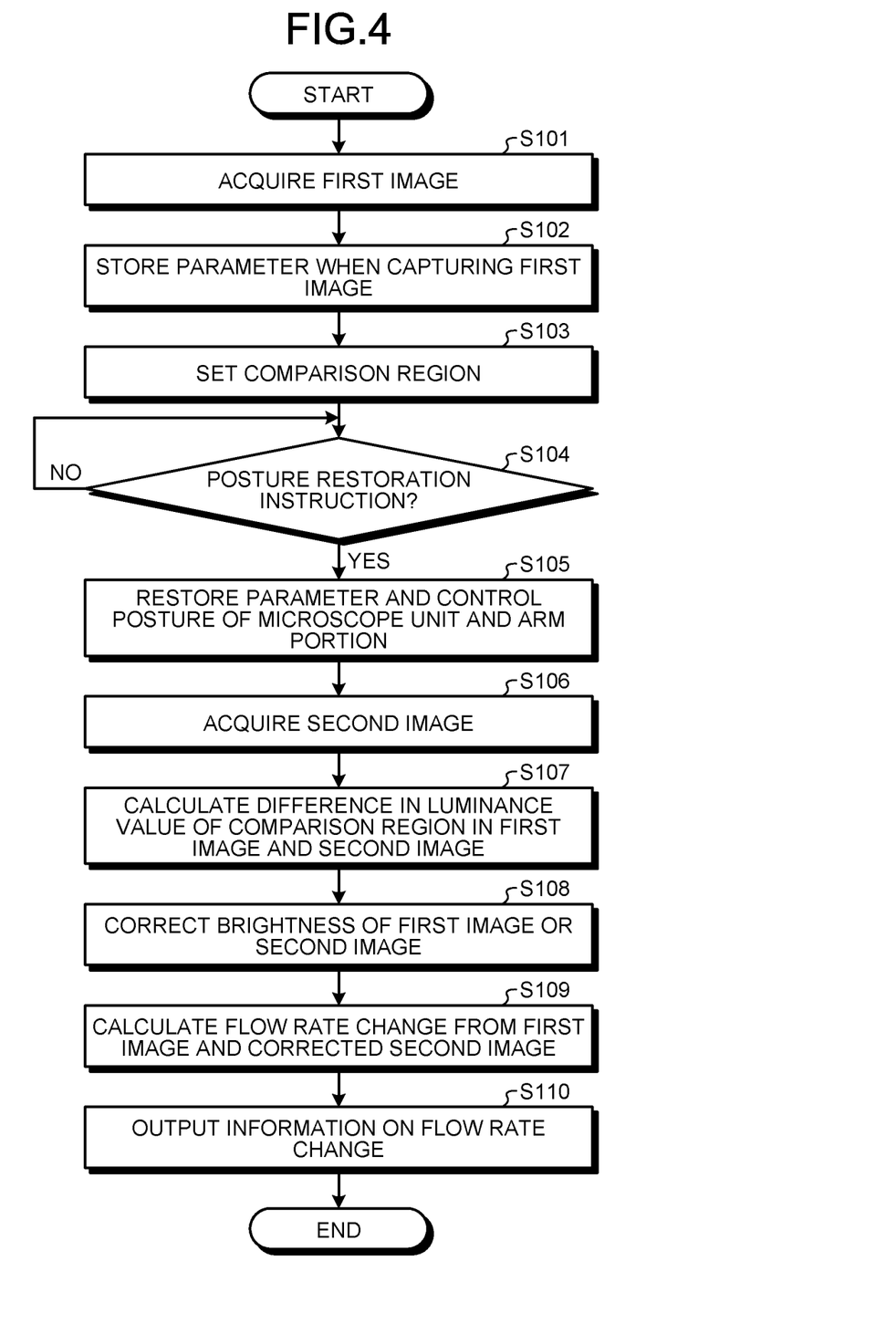
FIG. 4 is a flowchart illustrating a flow of a process performed by the control device of the medical observation system according to the first embodiment.

Subsequently, an image acquisition process performed by the control device 3 will be described with reference to FIGS. 4 to 6. FIG. 4 is a flowchart illustrating a flow of a process performed by the control device of the medical observation system according to the first embodiment. The flowchart illustrated in FIG. 4 illustrates an example in which the blood flow rate change is measured from the images before and after surgery by IRI.

First, the control unit 37 acquires a first image (a first medical image) before surgery by capturing an image using the microscope unit 7 (Step S101). At this time, the image processing unit 32 generates the first image based on an imaging signal. When the image is captured by the microscope unit 7, the control unit 37 stores a restoration parameter for an imaging condition (a first imaging condition) at the time of capturing the first image by the restoration setting unit 31.

In Step S102 following Step S101, the restoration setting unit 31 stores the restoration parameter by storing the restoration parameter at the imaging time point (the storage instruction time point from the control unit 37) in the storage unit 36.

The restoration setting unit 31 sets a comparison region in the generated first image so as to compare a luminance value with an image (a second image to be described later) after surgery (Step S103). The comparison region may be input and set by a user through the input unit 35 or may be set by a predetermined condition, for example, a predetermined position with respect to a viewing angle or a region in which luminance values of all pixels in a region to be set are equal to or smaller than a threshold value.

Figure 5:
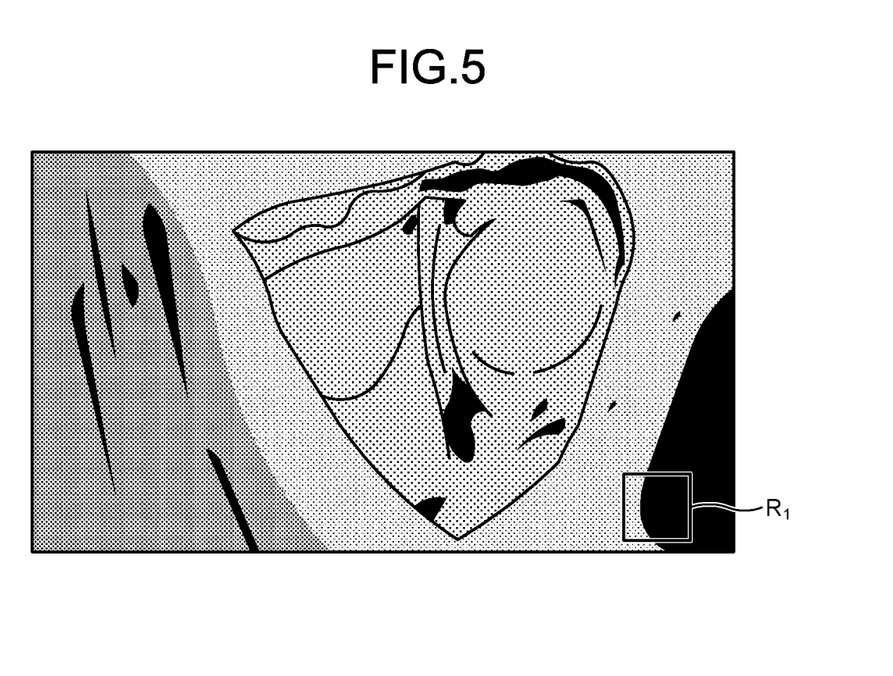
FIG. 5 is a diagram schematically illustrating an example of an image (a first image) before surgery.

FIG. 5 is a diagram schematically illustrating an example of an image (a first image) before surgery. Additionally, an example of a 2D image will be described as an example, but an operator actually observes a 3D image.

As illustrated in FIG. 5, a comparison region $R_1$ is set at the right lower position of the first image. The comparison region $R_1$ is set to, for example, a region in which brightness or shape does not change even after surgery other than a surgical site in the first image.

Then, surgery is performed by the operator. During this time, the control unit 37 checks whether or not a posture restoration instruction is input in order to restore the posture of each arm portion and the position of the microscope unit 7 (Step S104). The control unit 37 repeatedly checks whether or not the instruction is input when there is no input of the posture restoration instruction (Step S104: No). In contrast, when an operator inputs the posture restoration instruction through the input unit 35 after surgery, the control unit 37 determines that there is an input of the posture restoration instruction (Step S104: Yes) and proceeds to Step S105.

In Step S105, the restoration setting unit 31 reads out the restoration parameter stored in the storage unit 36 and restores the imaging condition or the position of the microscope unit 7. The control unit 37 sets a second imaging condition based on the restoration parameter read out by the restoration setting unit 31 and rotates the first joint portion 11 to the sixth joint portion 16 around the respective axes so that the position of the microscope unit 7 is restored and the imaging condition of the microscope unit 7 is set based on the restoration parameter.

Then, the control unit 37 acquires a second image (a second medical image) after surgery by capturing an image by the microscope unit 7 in the restored state (Step S106). At this time, the image processing unit 32 generates the second image based on an imaging signal.

Figure 6:
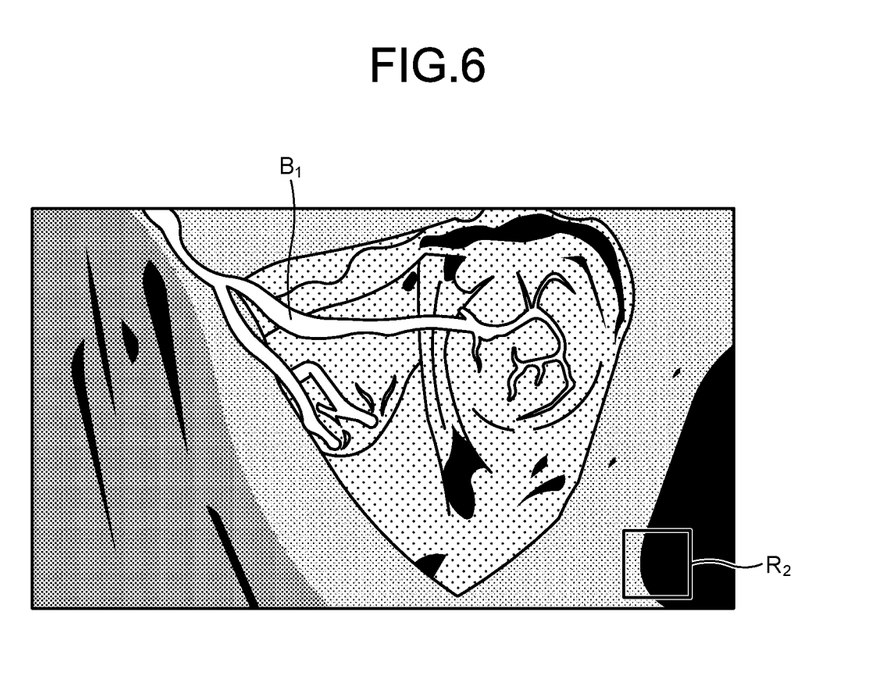
FIG. 6 is a diagram schematically illustrating an example of an image (a second image) after surgery.

FIG. 6 is a diagram schematically illustrating an example of an image (a second image) after surgery. As illustrated in FIG. 6, blood is drawn by ICG on the second image after surgery (see a region $B_1$). Further, a comparison region $R_2$ is set at a position corresponding to the first image in the second image.

In Step S107 following Step S106, the correction unit 33 calculates a difference between the luminance value of the comparison region $R_1$ in the first image and the luminance value of the comparison region $R_2$ in the second image.

Then, the correction unit 33 corrects the brightness of the first image or the second image based on the difference (Step S108). In the first embodiment, the correction unit 33 corrects the brightness of the second image based on the difference. The correction unit 33 corrects the brightness of the second image by adjusting a gain value based on, for example, a difference value. Additionally, the correction unit 33 may correct the brightness of the first image or may correct the brightness of each of the first image and the second image.

In Step S109 following Step S108, the change amount calculation unit 34 calculates a difference in brightness (luminance value) for each corresponding pixel as the blood flow rate change amount from the first image and the second image corrected by the correction unit 33. Additionally, the change amount calculation unit 34 may calculate the change amount for each pixel group forming a group with a preset number of pixels and pixel positions. In this case, a difference between the representative values of the luminance values of the pixels constituting the pixel group is calculated. The representative value is an average value, a mode value, a maximum value, a minimum value, or the like.

Then, the control unit 37 outputs information on the blood flow rate change amount calculated in Step S109 (Step S110). At this time, the image processing unit 32 applies a color based on the change amount and generates a superimposed image in which the color is superimposed on the first image or the second image at a corresponding position or a display image in which the change amount is represented by a numerical value as information on the change amount.

Figure 7:
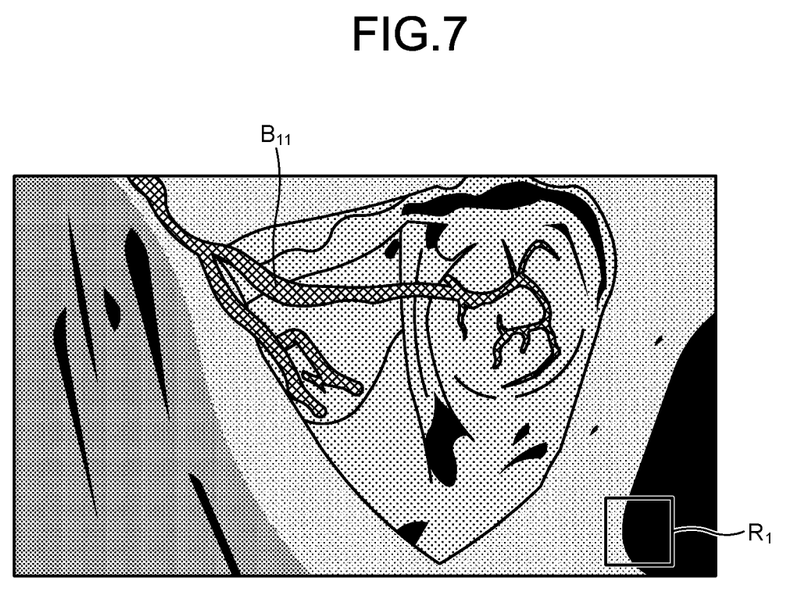
FIG. 7 is a diagram schematically illustrating an example of a measurement result display image.

FIG. 7 is a diagram schematically illustrating an example of a measurement result display image. FIG. 7 illustrates an image in which a color is superimposed based on a difference in luminance value between the first image (see FIG. 5) and the second image (see FIG. 6). In FIG. 7, the color of the superimposed region (region $B_{11}$) is indicated by hatching. As illustrated in FIG. 7, it is possible to check a change in the blood flow before and after surgery by superimposing a color based on a difference in the luminance value. Additionally, the color or shading is different based on the change amount in the superimposed region (region $B_{11}$).

In the above-described first embodiment, since the first comparison region is set on one image and the brightness (the luminance value) of the first comparison region is compared with the brightness (the luminance value) of the second comparison region at a position corresponding to the first comparison region in the other image so as to adjust the brightness of the image in a configuration in which the imaging timings are different, the position of the microscope unit 7 in the subsequent image is restored to a position in which the previous image is captured, and the captured images are compared so as to measure the change amount, brightness may be compared as images with the same brightness of two images. According to the first embodiment, it is possible to accurately compare the relative brightness of the images acquired at different timings.

Second Embodiment

Figure 8:
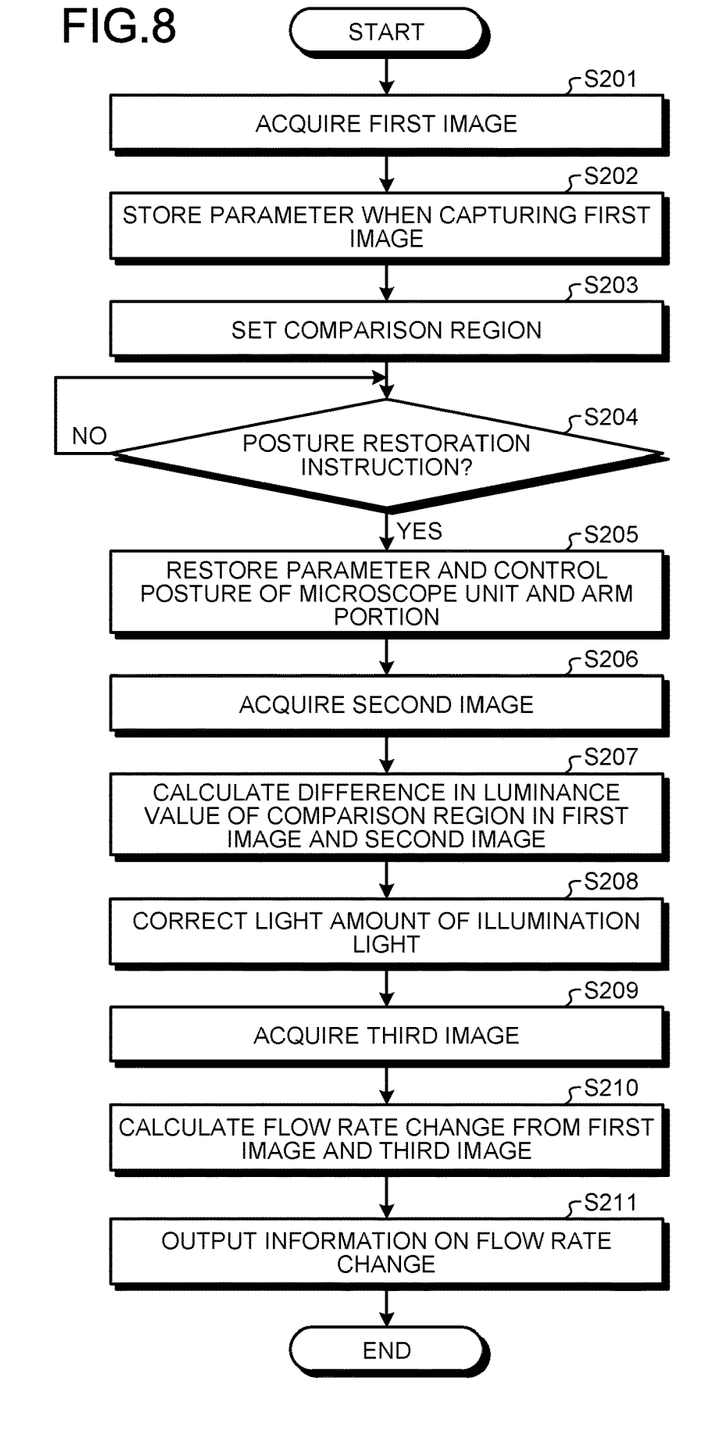
FIG. 8 is a flowchart illustrating a flow of a process performed by a control device of a medical observation system according to a second embodiment.

Next, a second embodiment will be described with reference to FIG. 8. FIG. 8 is a flowchart illustrating a flow of a process performed by a control device of a medical observation system according to the second embodiment. Since the medical observation system according to the second embodiment has the same configuration as that of the medical observation system 1 of the first embodiment, a description thereof will be omitted. Hereinafter, a process different from the first embodiment will be described. The flowchart illustrated in FIG. 8 illustrates an example of measuring a blood flow rate change from images before and after surgery by IRI similarly to the first embodiment.

First, the control unit 37 acquires the first image before surgery by capturing an image using the microscope unit 7 (Step S201). Then, the restoration setting unit 31 stores the restoration parameter by storing the restoration parameter at the imaging time point (the storage instruction time point from the control unit 37) in the storage unit 36 (Step S202). The restoration setting unit 31 sets the comparison region in the generated first image so as to compare the luminance value with the image (the second image) after surgery (Step S203).

Then, surgery is performed by the operator. During this time, the control unit 37 checks whether or not a posture restoration instruction is input in order to restore the posture of each arm portion and the position of the microscope unit 7 (Step S204). The control unit 37 repeatedly checks whether or not the instruction is input when there is no input of the posture restoration instruction (Step S204: No). In contrast, when an operator inputs the posture restoration instruction through the input unit 35 after surgery, the control unit 37 determines that there is an input of the posture restoration instruction (Step S204: Yes) and proceeds to Step S205.

In Step S205, the restoration setting unit 31 reads out the restoration parameter stored in the storage unit 36 and restores the imaging condition or the position of the microscope unit 7. Then, the control unit 37 acquires the second image after surgery by capturing an image using the microscope unit 7 in the restored state (Step S206).

In Step S207 following Step S206, the correction unit 33 calculates a difference between the luminance value of the comparison region in the first image and the luminance value of the comparison region in the second image.

Then, the correction unit 33 corrects the light amount of illumination light based on the difference (Step S208). In the second embodiment, the correction unit 33 corrects the illuminance of the light source based on the difference so as to be the same as the brightness of the first image. The correction unit 33 corrects the illuminance of the light source by adjusting an instruction value of the illuminance (brightness) based on, for example, the difference value.

The control unit 37 acquires the third image after surgery by capturing an image using the microscope unit 7 by the illumination light of which the illuminance of the light source is corrected (Step S209).

In Step S210 following Step S209, the change amount calculation unit 34 calculates a difference in brightness (luminance value) for each pixel position as the blood flow rate change amount from the first image and the acquired third image.

Then, the control unit 37 outputs information on the blood flow rate change amount calculated in Step S210 (Step S211). At this time, information on the change amount is provided by the image processing unit 32 as a superimposed image (see FIG. 7) in which a color is applied based on the change amount and is superimposed at a corresponding position on the first image or the second image or a display image in which the change amount is indicated by a numerical value.

In the above-described second embodiment, since the first comparison region is set one image, the brightness (the luminance value) of the first comparison region is compared with the brightness (the luminance value) of the second comparison region at a position corresponding to the first comparison region in the other image, and the illuminance of the light source is corrected based on a comparison result so as to adjust the brightness of the image in a configuration in which the imaging timings are different, the position of the microscope unit 7 in the subsequent image is restored to a position in which the previous image is captured, and the captured images are compared so as to measure the change amount, the images may be compared by adjusting the brightness of the obtained images. According to the second embodiment, it is possible to accurately compare the relative brightness of the images acquired at different timings.

Additionally, in the second embodiment, the third image may be acquired in Step S209, the luminance value of the third image may be compared with the luminance value of the first image, and the illumination light adjustment process after Step S207 may be repeated.

Further, in the second embodiment, an example in which the correction unit 33 corrects the illuminance of the light source based on the difference has been described. However, a parameter which does not change a viewing angle such as a gain process in the imaging element, a shutter speed, and an aperture value of a lens may be corrected or two or more parameters of the above-described parameters including the illuminance of the light source may be corrected.

Third Embodiment

Figure 9:
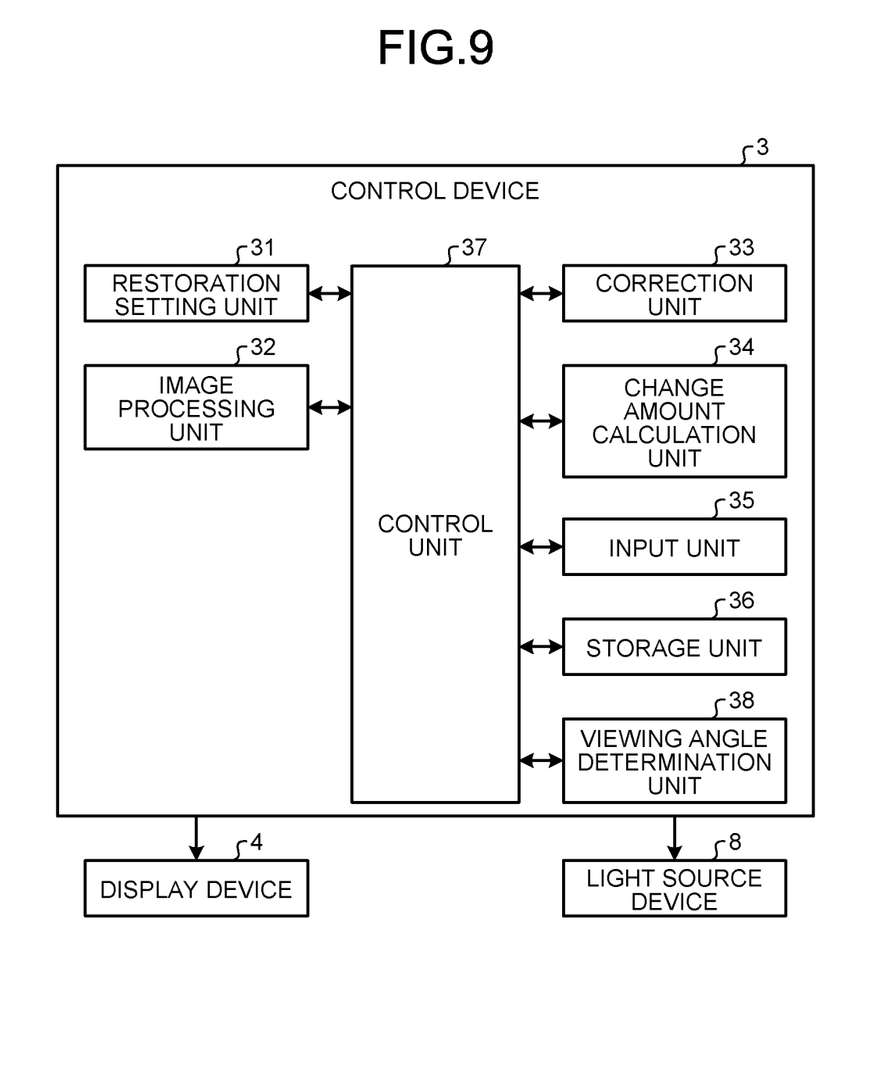
FIG. 9 is a block diagram illustrating a configuration of a control device of a medical observation system according to a third embodiment.

Next, a third embodiment will be described with reference to FIGS. 9 and 10. Since the third embodiment is the same as the above-described embodiment except that a control device 3A is provided instead of the control device 3 of the first embodiment, a description of a configuration or the like other than the control device 3A will be omitted.

The control device 3A includes the restoration setting unit 31, the image processing unit 32, the correction unit 33, the change amount calculation unit 34, the input unit 35, the storage unit 36, the control unit 37, and a viewing angle determination unit 38. The configuration of the control device 3A is the same as that of the control device 3 except that the viewing angle determination unit 38 is added. Hereinafter, the viewing angle determination unit 38 which is a configuration different from the first embodiment will be described.

The viewing angle determination unit 38 compares a viewing angle shift amount with a threshold value by detecting the position of the viewing angle of the other image in which the imaging position or the like is restored with respect to the viewing angle of one image in the images captured at different timings. The storage unit 36 stores a shift amount which is allowed with respect to a difference in viewing angle as a threshold value in advance.

Figure 10:
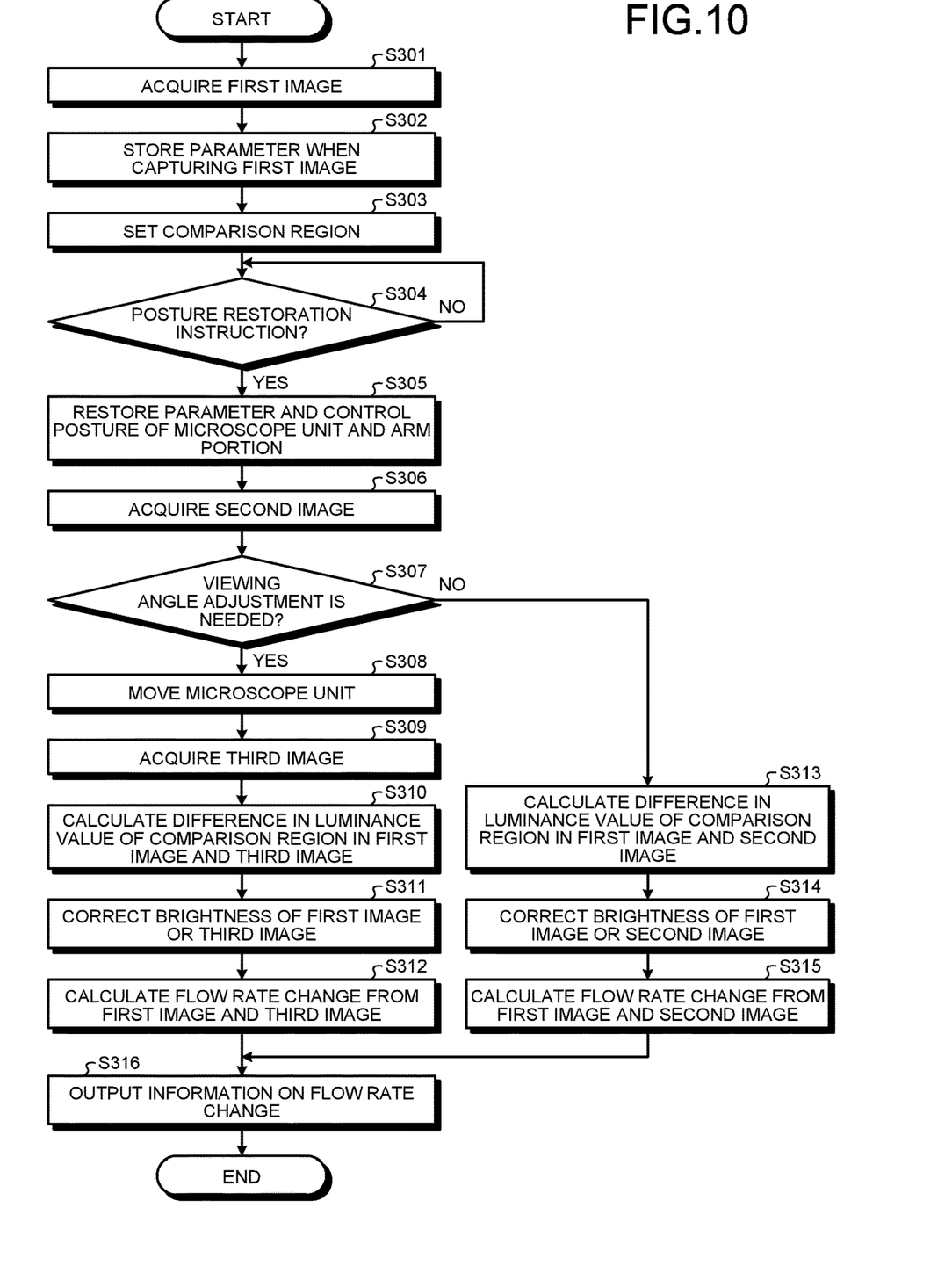
FIG. 10 is a flowchart illustrating a flow of a process performed by the control device of the medical observation system according to the third embodiment.

FIG. 10 is a flowchart illustrating a flow of a process performed by the control device of the medical observation system according to the third embodiment. The flowchart illustrated in FIG. 10 illustrates an example in which the blood flow rate change is measured from the images before and after surgery in IRI similarly to the first embodiment.

First, the control unit 37 acquires the first image before surgery by capturing an image using the microscope unit 7 (Step S301). Then, the restoration setting unit 31 stores the restoration parameter by storing the restoration parameter at the imaging time point (the storage instruction time point from the control unit 37) in the storage unit 36 (Step S302). The restoration setting unit 31 sets the comparison region in the generated first image so as to compare the luminance value with the image (the second image) after surgery (Step S303).

Then, surgery is performed by the operator. During this time, the control unit 37 checks whether or not a posture restoration instruction is input in order to restore the posture of each arm portion and the position of the microscope unit 7 (Step S304). The control unit 37 repeatedly checks whether or not the instruction is input when there is no input of the posture restoration instruction (Step S304: No). In contrast, when an operator inputs the posture restoration instruction through the input unit 35 after surgery, the control unit 37 determines that the posture restoration instruction is input (Step S304: Yes) and proceeds to Step S305.

In Step S305, the restoration setting unit 31 reads out the restoration parameter stored in the storage unit 36 and restores the imaging condition or the position of the microscope unit 7. Then, the control unit 37 acquires the second image after surgery by capturing an image using the microscope unit 7 in the restored state (Step S306).

In Step S307 following Step S306, the viewing angle determination unit 38 detects a difference between the viewing angle of the first image and the viewing angle of the second image and determines whether or not the viewing angle needs to be adjusted. The viewing angle determination unit 38 calculates a viewing angle shift amount by combining the viewing angle of the first image with the viewing angle of the second image using a known method such as pattern matching. The viewing angle determination unit 38 calculates the shift amount in the viewing angle shift direction. The viewing angle determination unit 38 compares the calculated shift amount with the threshold value. When the shift amount is larger than the threshold value (Step S307: Yes), it is determined that the viewing angle needs to be adjusted and the routine proceeds to Step S308.

The control unit 37 adjusts the position of the viewing angle of the microscope unit 7 for capturing by moving the arm portion and the microscope unit 7 based on the shift amount calculated by the viewing angle determination unit 38 (Step S308). At this time, the optical system inside the microscope unit 7 is moved if necessary. Then, the control unit 37 acquires the third image after surgery by capturing an image using the microscope unit 7 in the restored state (Step S309).

In Step S310 following Step S309, the correction unit 33 calculates a difference between the luminance value of the comparison region in the first image and the luminance value of the comparison region at a position corresponding to the comparison region of the first image in the third image.

Then, the correction unit 33 corrects the brightness of the first image or the third image based on the difference (Step S311). In the third embodiment, the correction unit 33 corrects the brightness of the third image based on the difference similarly to the first embodiment.

In Step S312 following Step S311, the change amount calculation unit 34 calculates a difference in brightness (luminance value) for each pixel position as the blood flow rate change amount from the first image and the third image corrected by the correction unit 33.

Meanwhile, in Step S307, the correction unit 33 compares the calculated shift amount with the threshold value. When the shift amount is the threshold value or less (Step S307: No), it is determined that the viewing angle does not need to be adjusted and the routine proceeds to Step S313.

In Step S313, the correction unit 33 calculates a difference between the luminance value of the comparison region in the first image and the luminance value of the comparison region in the second image. The correction unit 33 corrects the brightness of the first image or the second image based on the difference (Step S314). Then, the change amount calculation unit 34 calculates a difference in brightness (luminance value) for each pixel position as the blood flow rate change amount from the first image and the second image corrected by the correction unit 33 (Step S315).

The control unit 37 outputs information on a change amount of blood flow rate calculated in Step S312 or S315 (Step S316). At this time, information on the change amount is provided by the image processing unit 32 as a superimposed image (see FIG. 7) in which a color is applied based on the change amount and is superimposed at a corresponding position on the first image or the second image or a display image in which the change amount is indicated by a numerical value.

In the above-described third embodiment, since the first comparison region is set on one image and the brightness (the luminance value) of the first comparison region is compared with the brightness (the luminance value) of the second comparison region at a position corresponding to the first comparison region in the other image so as to adjust the brightness of the image in a configuration in which the imaging timings are different, the position of the microscope unit 7 in the subsequent image is restored to a position in which the previous image is captured, and the captured images are compared so as to measure the change amount, brightness may be compared as images with the same brightness of two images. According to the third embodiment, it is possible to accurately compare the relative brightness of the images acquired at different timings.

Further, in the third embodiment, since the viewing angle is adjusted to capture an image again when it is determined that the viewing angle of the image (the second image) captured by the restoration is shifted from the viewing angle of the image (the first image) before restoration, it is possible to output a measurement result while suppressing the omission of the measurement position with respect to the first image.

So far, a mode carrying out the disclosure has been described, but the disclosure is not limited to the above-described embodiments. For example, the support portion 6 may have at least one set of two arm portions and a joint portion that rotatably connects one of the two arm portions to the other thereof.

Additionally, in the processes of the first to third embodiments, the first image, the second image, and the third image with the special light may be acquired after the focusing process is performed with the white light. By performing the focusing process with white light, an image clearly focused on the observation object may be obtained as compared with light in a wavelength band of special light such as IRI.

Further, the medical observation apparatus may be disposed so as to be suspended from a ceiling of an installation location.

Further, in the first to third embodiments, an example in which the support portion 6 supports the microscope unit 7 has been described, but the support portion 6 may support a member having an imaging configuration instead of the microscope unit 7. For example, the support portion 6 may hold a rigid endoscope at the front end or may hold a front end of a flexible endoscope. When the support portion 6 holds the endoscope, the base portion 5 and the support portion 6 function as endoscope holders.

As described above, the disclosure may include various embodiments and the like without departing from the technical spirit described in the claims.

As described above, the medical observation system according to the present disclosure is useful for accurately comparing the relative brightness of images acquired at different timings.

According to the present disclosure, it is possible to accurately compare the relative brightness of the images acquired at different timings.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation control device comprising:
a memory configured to store a parameter for a first imaging condition including a position of an imager at a first time of capturing a first medical image of an observation object; and
circuitry configured to
acquire the first medical image;
determine a first surgical site in the first medical image, wherein the first surgical site is affected by a medical imaging contrast agent;
set a first comparison region in the first medical image separate from the first surgical site and unaffected by the medical imaging contrast agent;
restore the parameter for the first imaging condition as a second imaging condition for capturing a second medical image of the observation object at a second time, after the first time and after surgery, the second imaging condition being under a same wavelength band as the first imaging condition,
control the imager and a support configured to support the imager so as to capture the second medical image of the observation object under the second imaging condition,
acquire the second medical image,
compare a first luminance value of the first comparison region set in the first medical image captured at the first time with a second luminance value of a second comparison region set to a position corresponding to the first comparison region in the second medical image captured at the second time,
correct brightness of at least one of the first medical image and brightness of the second medical image based on a difference between the first luminance value and the second luminance value to generate a corrected first medical image and a corrected second medical image,
calculate a change amount between the first surgical site in the corrected first medical image and a second surgical site in the corrected second medical image, and
output a representation of the change amount.

2. The medical observation control device according to claim 1, wherein the circuitry is configured to correct the second imaging condition based on the difference.

3. The medical observation control device according to claim 2, wherein the circuitry is configured to correct at least one of illuminance of illumination light emitted from a light source configured to emit illumination light for illuminating an imaging region of the imager; a gain process of the imager; a shutter speed; and an aperture value of a lens.

4. The medical observation control device according to claim 1, wherein the circuitry is further configured to determine a difference in viewing angle by comparing a viewing angle of the first medical image with a viewing angle of the second medical image.

5. The medical observation control device according to claim 1, wherein the circuitry is further configured to calculate a change amount of brightness between the first medical image and the second medical image after the correction.

6. The medical observation control device according to claim 1 wherein the circuitry is configured to output a numerical value corresponding to the change amount to a display.

7. The medical observation control device according to claim 1 wherein the circuitry is configured to output an image corresponding to the change amount to a display to be superimposed on at least one the first medical image and the second medical image.

8. The medical observation control device according to claim 1 wherein the change amount is a blood flow change amount.

9. The medical observation control device according to claim 1, wherein the second time is after an operation has been performed on the observation object.

10. The medical observation control device according to claim 1, wherein the circuitry is configured to set the first comparison region based on a predetermined condition.

11. The medical observation control device according to claim 10, wherein the predetermined condition includes a predetermined position with respect to a viewing angle or a region in which luminance values of all pixels in the region to be set are equal to or smaller than a threshold value.

12. A medical observation system comprising:
a medical observation apparatus configured to capture an image of an observation object, the medical observation apparatus including
an imager configured to capture the image of the observation object, and
a support configured to support the imager; and
a control device configured to control the medical observation apparatus electrically, the control device including
memory configured to a store a parameter for a first imaging condition including a position of the imager at a first time of capturing a first medical image of the observation object,
circuitry configured to
acquire the first medical image;
determine a first surgical site in the first medical image, wherein the first surgical site is affected by a medical imaging contrast agent;
set a first comparison region in the first medical image separate from the first surgical site and unaffected by the medical imaging contrast agent;
restore the parameter for the first imaging condition as a second imaging condition for capturing a second medical image of the observation object at a second time, after the first time and after surgery, the second imaging condition being under a same wavelength band as the first imaging condition,
control the imager and the support so as to capture the second medical image of the observation object under the second imaging condition,
compare a first luminance value of the first comparison region set in the first medical image captured at the first time with a second luminance value of a second comparison region set to a position corresponding to the first comparison region in the second medical image captured at the second time,
correct brightness of at least one of the first medical image and brightness of the second medical image based on a difference between the first luminance value and the second luminance value to generate a corrected first medical image and a corrected second medical image,
acquire the second medical image;
calculate a change amount between the first surgical site in the corrected first medical image and a second surgical site in the corrected second medical image, and
superimpose a representation of the change amount on one of the first medical image and the second medical image.

13. The medical observation system according to claim 12, further comprising: a light source configured to emit illumination light for illuminating an imaging region of the imager, wherein the circuitry is configured to correct at least one of illuminance of illumination light emitted from the light source; a gain process of the imager; a shutter speed; and an aperture value of a lens.

14. The medical observation system according to claim 12, further comprising a display, wherein the circuitry is configured to output the representation to the display and the display displays the representation.

15. The medical observation system according to claim 14, wherein the representation is a numerical value corresponding to the change amount to the display and the display displays the numerical value.

16. The medical observation system according to claim 14, wherein the representation is an image corresponding to the change amount to the display and the display superimposes the image on at least one the first medical image and the second medical image.

17. The medical observation system according to claim 12, wherein the change amount is a blood flow change amount.

* * * * *